(12) United States Patent  (10) Patent No.:  US 6,329,152 B1
Patterson  (45) Date of Patent:  Dec. 11, 2001

(54) PROCESS FOR DETECTING LOW ABUNDANCE RNA IN INTACT CELLS

(76) Inventor: Bruce K. Patterson, 211 W. St. Paul, Apt. 3, Chicago, IL (US) 60614

( * ) Notice: Subject to any disclaimer, the term of this patent is extended or adjusted under 35 U.S.C. 154(b) by 0 days.

(21) Appl. No.: 09/728,832

(22) Filed: Nov. 30, 2000

(51) Int. Cl.$^7$ .............................. C12Q 1/68; C07H 21/04
(52) U.S. Cl. ........................................... 435/6; 536/24.32
(58) Field of Search .................... 435/6, 69.1; 536/24.32

(56) References Cited

PUBLICATIONS

Patterson BK et al. Detection of HIV–1 DNA and mRNA in individual cells by PCR–driven in situ hybridization and flow cytometry. Science, 260: 976–979, 1993.*

Mosiman et al. Reducing cellular Autofluorescence in flow cytometry: an in situ method. Cytometry, 30: 151–156, 1997.*

Hougaard DM et al. Non–radioactive in situ hybridization for mRNA with emphasis on the use of oligodeoxynucleotide probes. Histochem Cell Biol., 108: 335–344, 1997.*

* cited by examiner

*Primary Examiner*—Eggerton A. Campbell
*Assistant Examiner*—Suryprabha Chundru
(74) *Attorney, Agent, or Firm*—Niro, Scavone, Haller & Niro

(57) ABSTRACT

The present invention provides a process for detecting the presence of a target mRNA in an intact cell. The process includes the steps of (a) fixing and permeabilizing with a non- or weakly-crosslinking reagent the cell in the presence of a plurality of oligonucleotide probes, wherein each probe (i) contains about 15 to about 30 nucleotides, (ii) is labeled with a detectable marker, (iii) has a matched Tm of greater than about 60° C., and (iv) specifically hybridizes to a different contiguous region of an open reading frame in the target mRNA with the provisos that each probe does not hybridize to itself, does not hybridize to any other probe and does not hybridize to a contiguous sequence of $(A)_{n9}$ $(C)_{n9}$ $(G)_n$ or $(U)_n$ in the target mRNA where n is an integer greater than 5; (b) removing unhybridized probes from the cell; and (c) measuring the detectable label in the cell.

22 Claims, 1 Drawing Sheet

PROCESS FOR DETECTING LOW ABUNDANCE RNA IN INTACT CELLS

TECHNICAL FIELD OF THE INVENTION

The field of this invention is cellular RNA detection. More particularly, the present invention pertains to a process for detecting the presence of a specific target mRNA molecule present in low abundance in intact cells.

BACKGROUND OF THE INVENTION

Many approaches have been used to identify nucleic acids within cells and tissues. In situ PCR (ISPCR) is extremely sensitive as this technique has been shown to detect single copy DNA and low abundance RNA. ISPCR, however, yields no information on the starting target copy number and thermal amplification of cells increases cellular autofluorescence five-fold. Conversely, in situ hybridization allows quantification of the starting copy number though the sensitivity ranges between 100–1000 copies. Further, the current art of in situ hybridization uses compounds such as dextran sulfate, acetic anhydride, polyethylene glycol (PEG), hydrochloric acid, and others that either fluoresce or increase cellular autofluorescence. In sum, compounds that either fluoresce in the range of the reporter fluorescent dye or increase cellular autofluorescence decrease signal to noise (SNR) and sensitivity. The present invention provides a method to detect and quantify intracellular nucleic acids with a sensitivity between 3–100 copies. This level of sensitivity is acheived by using a novel combination of non- or weakly crosslinking fixatives and exclusion of autofluorescent compounds commonly used for in situ hybridization. In addition, this method allows simultaneous analysis of cell surface markers including but not limited to phenotypic markers, activation markers, functional markers, and antigens associated with cell death injury.

The optimal detection system should be able to detect a very few copies of a particular target with a broad, linear range for quantification. In addition, this detection scheme should allow simultaneous multiparameter (immunophenotypic) analysis and should be adaptable for use on multiple detection platforms (flow cytometer, image analysis). Last, this optimal test should be easy to perform with high throughput capabilities. The most important determinants of successful in situ hybridization experiments are access to target and signal to noise ratio (SNR). Access to intracellular targets, whether protein or nucleic acids, has always been a challenge. In addition, proteins bound to nucleic acids provide additional obstacles for in situ detection. The approaches to overcome these obstacles depend on the cells or tissue. Cells in suspension or adhered to slides are generally intact. Access to nucleic acids in cells involves permeabilization of the cell membrane and removal of protein bound to nucleic acids. Many agents have been used to permeabilize and many have been commercialized as "fix and perm" combinations. In the past, methanol was used to extract lipids, protease were used to digest membrane associated proteins, and saponin was used to extract membrane associated cholesterol. Methanol, however, was a poor fixative and protease treatment was temperamental with a fine line between optimal use and complete obliteration of cells, and saponin was required in all solutions following the fixation step to maintain permeability.

The classic model systems illustrating sensitivity (high SNR) of detection schemes are human papilloma virus infection and HIV infection. The human papilloma virus (HPV) infected cell lines, SiHa and Caski, contain different number of HPV copies. SiHa cells contain two copies of HPV DNA and Caski cells contain about 300 copies of HOV DNA. In situ hybridization can detect HPV DNA in Caski cells but not SiHa cells. In situ PCR, on the other hand, can detect HPV DNA in both cell lines. In situ PCR, however, is inconsistent, technically difficult, and has a low throughput.

Similarly, the HIV life cycle in cells presents the ultimate challenge for gene detection. Determinants of viral replication including expression of unspliced HIV mRNA and plasma free virus has led to the use of virologic markers as a measure of disease status and therapeutic efficacy. A marked increase in the ratio of unspliced to spliced HIV mRNA, as might occur during the shift from latent to productive infection, precedes precipitous drops in CD4 count. Plasma viral load has been shown to correlate with disease progression and has been used to determine HIV kinetic in vivo. These measurements, however, fail to provide information on the cell type of origin, a weakness considering, the effect of HIV gene expression on cell function, the role of infected cells in transmission and dissemination, and the therapeutic potential of blocking cell-type specific coreceptors.

BRIEF SUMMARY OF THE INVENTION

The present invention provides a process for detecting the presence of a target mRNA in an intact cell. The process includes the steps of (a) preserving and permeabilizing the cell with a non or weakly crosslinking fixative in the presence of a plurality of oligonucleotide probes, wherein each probe (i) contains about 6 to about 30 nucleotides, (ii) is labeled with a detectable marker, (iii) has a matched Tm of greater than about 60° C., and (iv) specifically hybridizes to a different contiguous region of an open reading frame in the target mRNA with the provisos that each probe does not hybridize to itself, does not hybridize to any other probe and does not hybridize to a contiguous sequence of $(A)_n (C)_n (G)_n$ or $(U)_n$ in the target mRNA where n is an integer greater than 5; (b) removing unhybridized probes from the cell; and (c) measuring the detectable label in the cell.

The process can be used to detect target mRNA in a cell in a copy number of from about 3 to about 100. More particularly, the process can be used to detect mRNA present in copy numbers of from about 3 to about 100, from about 3 to about 50 and more preferably in copy numbers from about 3 to about 25.

The process can be used to detect mRNA that is indigenous to the cell or present in the cell as a result of introduction from an outside source such as gene transformation or viral infection. In a preferred embodiment, the process is used to detect cellular mRNA such as glyceraldehyde-3-phosphate dehydrogenase (GAPDH).

The process can be used with any cell from any animal. The process is particularly suited for detection of mRNA in white blood cells of human patients. A preferred white blood cell is a lymphocyte such as a T-lymphocyte.

The detectable label used in accordance with the process is preferably a fluorescent label such as 6-carboxyfluorescein. Each of the plurality of oligonucleotide probes is labeled with the same fluorescent label or in another embodiment different fluorescent labels.

The present process can be used simultaneously with other processes such as a process for detecting the presence of an immunogenic or molecular marker of cell function in the cell. In preferred embodiments, the marker is a marker of cell phenotype, cell activation, or cell death.

DESCRIPTION OF THE DRAWINGS

These and other features, objects and advantages of the present invention will become apparent from the following description and drawings wherein like reference numerals represent like elements in several views, and in which.

DESCRIPTION OF THE INVENTION

Figure 1:
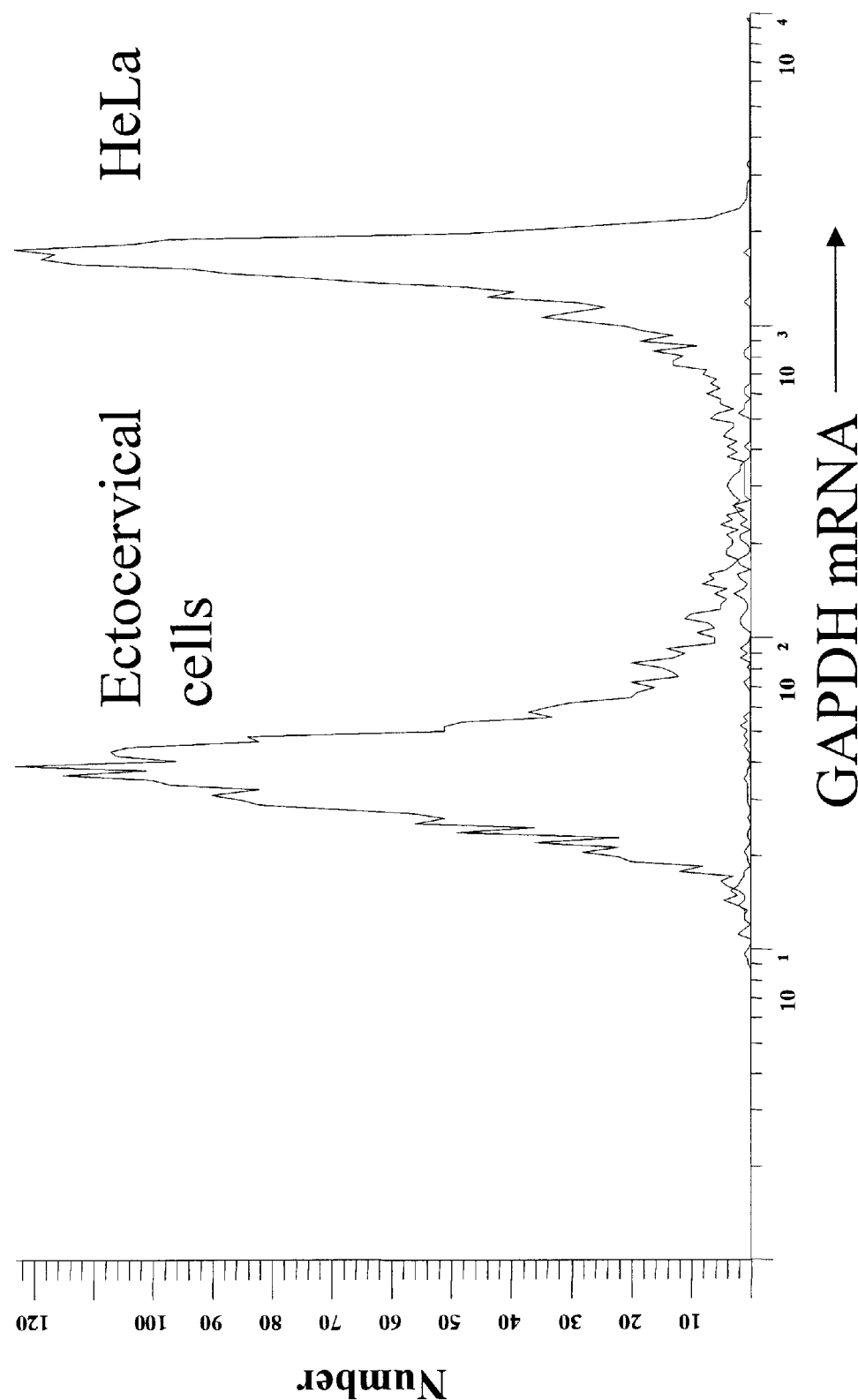
FIG. 1 is a flow cytometry histogram showing detection of GAPDH mRNA using one embodiment of the present invention.

Set forth below is a description of what are currently believed to be the preferred embodiments or best examples of the invention claimed. Future and present alternatives and modifications to the preferred embodiments are contemplated. Any alternates or modifications in which insubstantial changes in function, in purpose, in structure or in result are intended to be covered by the claims of this patent.

The present invention provides a process for detecting the presence of low abundance mRNA in intact cell. The process can be used to detect mRNA that is present in cells at a copy number of between 3 and about 25. The process is particularly suited for detecting the presence of 3 to 15, 3 to 10, and even 3 to 5 copies of the RNA.

The process can be used to detect low abundance RNA in any cell, tissue, or cell extracted from tissue (fine needle aspiration) from any animal, including humans. The process can be used, for example, to detect mRNA in white blood cells of human patients. Any white blood cell can be used in the process. In one embodiment, the process is used to detect the presence of mRNA in lymphocytes and, in particular, T-lymphocytes.

The process can be used to detect any RNA in the cell. The detected mRNA can be indigenous to the cell and the result of gene expression. In an alternate embodiment, the mRNA is present in the cell as a result of transformation or infection. As shown in FIG. 1, the present process has been shown to be useful in detecting the presence of upregulated GAPDH mRNA resulting from activation of cells. Dysregulation of GAPDH expression has been described in cervical cancer.

To monitor drug and vaccine therapy in viral disease, more sensitive approaches are necessary. The present process is a unique and easy method to detect and quantify very low copy number genes in cells. The present process can detect low abundance viral mRNA especially those mRNAs expressed during viral reactivation (e.g. CMV IE1,2,3 mRNA, Epstein-Barr EBER1,2, hepatitis A, B, C, influenza, parainfluenza, respiratory syncytial virus, enterovirus, coxsackievirus A, B ebola virus and the like).

The process uses a plurality of oligonucleotide probes that hybridize to regions of the target mRNA. Preferably, the probes hybridize to regions of the open reading frame. Probes are designed based on the antisense sequence of target gene open reading frames. In the preferred embodiment, oligonucleotide probes have a matched Tm of greater than 60° C. Each probe contains between about 6 and 30 bases. The probes are designed to maximize the signal to noise ratio of detection. Thus, probes are designed and made such that they do not hybridize regions of mRNA that are common to all mRNA molecules. By way of example, the probes have sequences that do not hybridize to runs of poly-A, poly-C, poly-U, or poly-G. That is, none of the probes contain contiguous sequences of $(A)_n(G)_n(C)_n$ or $(T)_n$, where n is greater than 5. To further maximize the detection signal to noise ratio, probe sequences are designed such that the probes do not contain 5' guanosine. Still further, the probes do not hybridize to any other probe and each probe does not hybridize with itself. Each of the probes is designed to hybridize to a different region of the target mRNA. Preferably, the target region for each probe is separated by at least 5 bases from the target region of other probes. In this way, problems of energy transfer and dye quenching are minimized.

All that is needed to design a plurality of probes is knowledge of the nucleotide sequence of the target RNA. Probes are made using standard techniques (e.g., solid-phase synthesis) which are well known in the art. For some targets, sets of probe pluralities are commercially available (see the Examples hereinafter). Each probe in the plurality is labeled with a detectable marker. Preferably, the detectable marker is a marker capable of detection using light. An exemplary and preferred detectable label is fluorescent label. Fluorescent labels for oligonucleotides are well known in the art and include, for example, 5-carboxyfluorescein, or 6-carboxyfluorescein. Each of the probes in the plurality is labeled with the identical marker or, in another embodiment, a different marker. Each probe may also be labeled with one or more additional markers that serve to decrease background or increase signal. Means for labeling oligonucleotide probes with detectable (e.g., fluorescent) markers are well known in the art.

Once a plurality of probes is designed and made, the probes are exposed to the target mRNA in the cells. Exposure is accomplished by permeabilizing the cells in the presence of the probes. To enhance efficiency, the particular cell type of interest can be first separated and isolated from other cell types. Any method of isolating and separating the cells can be used so long as the method does not destroy the cell. Where the cells are white blood cells, separation using ficoll gradients can be used.

Permeabilization is accomplished by exposing the cells to a medium that contains a non- or weakly crosslinking permeabilization and fixing reagent. Permeabilization typically occurs at a temperature of from about 35° C. to about 45° C. for a period of time of from about 20 minutes to about 120 minutes. Following permeabilization, the cells are washed once in phosphate buffered saline (PBS) and once in 2×SSC. Probe hybridization is performed at about 43° C. for about 30–120 minutes in the presence of 5×SSC, 30% formamide, and yeast RNA. Post-hybridization washes consist of 1×SSC and 0.1% Triton X-100 for 5–10 minutes and 0.1% SSC/0.1% Triton X-100 for 15–30 minutes. The amount of detectable label in the cells can then be determined. Preferably, measurement of the detectable marker is accomplished using flow cytometry, laser confocal microscopy, fluorescence microscopy, fluorescence scanners and the like. The actual means of detecting depends on the nature of the detectable label.

Unlike other probe labeling strategies (e.g., nick translation, random primers and in vitro transcription), the present invention provides an exact number of fluorescent dye molecules per target copy. Using commercially available fluorescent dye standard beads, the exact number of mRNA copies within a cell can be determined from the number of fluorescent equivalents in the target positive cell. This number is then divided by the number of fluorescent dye equivalents in the probe (i.e., 80 fluorescein equivalents per copy of GAPDH) to provide copy number.

A process of one embodiment of the present invention can be used to detect patterns of gene expression by labeling random, small oligonucleotides (e.g. 6–10 random bases)

with different fluorescent labels such that the random association of the fluorescent labels with randomly expressed mRNAs would yield a distinct signature fluorescence profile for each specific cell type normal or abnormal. An instrument such as a flow cytometer would determine the fluorescence profile of a population of cells with a heterogeneous mixture of cells (e.g. blood, cervical cytology). In using this method of the present invention, a plurality of different fluorescent labels may be constructed for association with a plurality of different cell types. This, in turn, would allow for the detection of a plurality of cell types by using a cocktail of various markers and then examining for a specific mRNA profile known to be associated with a specific cell type.

A process of another embodiment of the present invention can be used in simultaneous conjunction with other procedures that measure markers of cell function such as immunogenic markers of phenotype, immunogenic markers of cells activation or molecular markers of cell death (apoptosis). Such markers of cell function and means for detecting those markers are well known in the art.

The process of the present invention is particularly useful in combination with the simultaneous measurement of immunophenotypic markers (e.g. CD4, CD14, CD68), cell surface receptors (e.g. CCR5, CXCR4, CCR3), cell activation markers (e.g. CD45RO, CD69, CD25), markers of cell death (apoptosis) (e.g. simultaneous in situ hybridization and TUNEL), and cell cycle markers (e.g. propidium iodide nuclear stain).

By way of example, the following protocol can be used to simultaneously measure mRNA using a process of this invention and immunogenic cell phenotype markers. Isolate mononuclear cells by layering on ficoll-hypaque. Label $1\times10^6$ cells with optimized concentrations of phycoerythrin (PE), ECD (energy coupled dye), or APC (allophycocyanin) conjugated antibodies in 100 µl total volume and incubate for 30 minutes at 4° C. Add 500 µl PBS, pH 7.4 to cells and centrifuge for 10 minutes at 300–600×g. Resuspend cells in 50 µl PermeaFix (Ortho Diagnosics, Raritan, N.J.) by dropwise addition with gentle vortexing. Incubate cells at ambient incubation temperature for at least 60 minutes and up to 18 hours. Add 500 µl PBS, pH 7.4 and centrifuge for 10 minutes at 300–600×g. Resuspend cell pellet in 500 µl 2×SSC and centrifuge for 10 minutes at 300–600×g. Remove as much supernatant as possible without disturbing the cell pellet. Resuspend cells in 50 µl hybridization buffer (5×SSC, 30% formamide, 100 µg/ml Herring sperm DNA) containing a cocktail of 5-carboxyfluorescein-labeled oligonucleotides specific for GAPGH mRNA (see probe formula). Hybridize probe to target for 30 minutes to 2 hours at 43° C. in a water bath. Add 500 µl wash solution A (1×SSC, 0.1% Triton X-100) B (preheated to 43° C.) to hybridization mix and centrifuge for 10 minutes at 300–600×g. Add 500 µl wash solution B (0.1×SSC, 0.1% Triton X-100) (preheated to 43° C.) to cells and incubate at 43° C. for 15–30 minutes. Centrifuge for 10 minutes at 300–600×g. Resuspend cells in PBS, pH 8.3. Analyze cells by flow cytometry, laser confocal microscopy, or fluorescence microscopy.

The Examples that follow illustrate specific embodiments of the present invention and are not limiting of the specification and claims in any way.

EXAMPLE 1

Simultaneous Detection of T-lymphocyte Activation Antigens and GAPDH mRNA.

Monoclonal antibodies have allowed researchers to define the cell types that comprise the human immune system. T-lymphocytes can be divided into complementary, non-overlapping populations predominantly based on functional activities. Lymphocytes can be divided into CD4 and CD8 positive populations. CD4 lymphocytes provide helper function for both the humoral and cellular components of the immune system and CD8 lymphocytes are the effector cells of the cell-mediated immune system. Within both the CD4 and CD8 positive populations, function can be determined by staining with a variety of monoclonal antibodies. An important distinction is made between the CD45RA population and CD45RO population. CD45RA lymphocytes are antigen naive and CD45RO respond well to recall antigens and have been labeled memory/activated T-lymphocytes.

The specific sequence for the marker that may be used in the detection of GAPDH mRNA is as follows:

```
gggaaggtgaaggtcggagtcaacg
ggtcgtattgggcgcctggtcacca
gcttttaactctggtaaagtggata
gccatcaatgacccctttcattgacc
tacatggtttacatgttccaatatg
acccatggcaaattccatggcaccg
gctgagaacgggaagcttgtcatca
aatcccatcaccatcttccaggagc
ccctccaaaatcaagtggggcgatg
gctgagtacgtcgtggagtccactg
ttcaccaccatggagaaggctgggg
ttgcagggggagccaaaagggtca
tctgcccctctgctgatgcccca
gtcatgggtgtgaaccatgagaagt
aacagcctcaagatcatcagcaatg
tgcaccaccaactgcttagcacccc
aaggtcatccatgacaactttggta
gaaggactcatgaccacagtccatg
actgccacccagaagactgtggatg
tccgggaaactgtggcgtgatggcc
gctctccagaacatcatccctgcct
ggcgctgccaaggctgtgggcaagg
cctgagctgaacgggaagctcactg
gccttccgtgtccccactgccaacg
gtggtggacctgacctgccgtctag
cctgccaaatatgatgacatcaaga
gtgaagcaggcgtcggagggccccc
ggcatcctgggctacactgagcacc
gtctcctctgacttcaacagcgaca
tcctccacctttgacgctggggctg
gccctcaacgaccactttgtcaagc
```

```
-continued tcctggtatgacaacgaatttggct aacagggtggtggacctcatggccc gcctccaaggagtaagacccctgga agccccagcaagagcacaagaggaa agaccctcactgctggggagtccct actcagtcccccaccacactgaatc tcctcacagttgccatgtagacccc gaggggagggggcctagggagccgca tcatgtaccatcaataaagtaccct
```

EXAMPLE 2

Simultaneous Detection of very Low Abundance mRNA and Cell Death/cell Cycle

A variety of methods have been developed to determine the state of a cell from the cell cycle (e.g. $G_1$-$G_2$ or $G_2$-M) to cell death (apoptosis). Cell cycle and apoptosis determination has important implications in diseases as diverse as cancer and HIV infection. To address these issues, a method to perform simultaneous cell cycle/apoptosis analysis was used by staining cellular DNA with the intercalating dye propidium iodide (5 $\mu$g/ml) with (apoptosis) (Hocscht 33342) or 7-AAD for example. Following staining the cells were washed, fixed/permeabilized, and hybridized as described above. This example provides information on the state of gene expression (GAPDH) when cells are potentially undergoing processes leading to cancer or cell death.

In addition, following cell isolation from blood or tissue, the cells may be resuspended in a volume of phosphate buffered saline, pH 7.4 (PBS) and stained with one or more directly conjugated antibodies labeled with a fluorescent dye different than but compatible with the fluorescent dye labeled oligonucleotides. These antibody labels for example could be phycoerythrin (PE), allophycocyanin (APC) and the like excluding PerCP which does not survive the thermal hybridization. Following incubation at 4 degrees C. for 20 minutes the excess antibodies are washed away using PBS and fixed as described.

While the preferred embodiments of the present invention have been illustrated and described, it will be understood by those of ordinary skill in the art that changes and other modifications can be made without departing from the invention in its broader aspects. Various features of the present invention are set forth in the following claims.

What is claimed is:

1. A process for detecting the presence of a target mRNA in an intact cell comprising:
   a. permeabilizing the cell in the presence of a plurality of different oligonucleotide probes, wherein each probe (i) contains about 15 to about 30 nucleotides, (ii) is labeled with a detectable maker, (iii) has a matched Tm of greater than about 60° C., and (iv) specifically hybridizes to a different contiguous region of an open reading frame in the target mRNA with the provisos that each probes does not hybridize to itself, does not hybridize to any other probe and does not hybridize to a contiguous sequence of $(A)_{n9}$ $(C)_{n9}$ $(G)_n$ or $(U)_n$ in the target mRNA where n is an integer greater than 5 to increase the detection signal of a target mRNA in an intact cell;
   b. removing unhybridized probes from the cell; and
   c. measuring the detectable label in the cell.

2. The process of claim 1 wherein the target mRNA is present in the cell in a copy number of from about 3 to about 100.

3. The process of claim 1 wherein the target mRNA is present in the cell in a copy number of from about 3 to about 25.

4. The process of claim 1 wherein the target mRNA is present in the cell in a copy number of from about 3 to about 10.

5. The process of claim 1 wherein the target mRNA is present in the cell in a copy number of from about 3 to about 5.

6. The process of claim 1 wherein the target mRNA is a cellular mRNA.

7. The process of claim 1 wherein the target mRNA is a viral mRNA.

8. The process of claim 6 wherein the viral mRNA is HIV mRNA, CMV mRNA or HPV mRNA.

9. The process of claim 1 wherein the cell is an epithelial cell.

10. The process of claim 1 wherein the cell is an endothelial cell.

11. The process of claim 1 wherein the cell is a liver cell.

12. The process of claim 1 wherein the cell is a neuronal cell.

13. The process of claim 1 wherein the cell is a hematopoeitic cell.

14. The process of claim 1 wherein the cell is a monocyte/macrophage cell.

15. The process of claim 1 wherein the cell is a dendritic cell.

16. The process of claim 1 wherein the cell is a leukocyte.

17. The process of claim 16 wherein the leukocyte is a lymphocyte.

18. The process of claim 17 wherein the lymphocyte is a T-lymphocyte.

19. The process of claim 1 wherein the detectable label is a fluorescent label.

20. The process of claim 19 wherein the fluorescent label is a 6-carboxyfluorescein.

21. The process of claim 1 further comprising simultaneously detecting the presence of an immunogenic or molecular marker of cell function in the cell.

22. The process of claim 21 wherein the marker is a marker of cell phenotype, cell activation, or cell death.

* * * * *